(12) United States Patent  
Hummer et al.

(10) Patent No.: US 11,061,009 B2  
(45) Date of Patent: Jul. 13, 2021

(54) CHEMICAL SENSOR DEVICES AND METHODS FOR DETECTING CHEMICALS IN FLOW CONDUITS, POOLS AND OTHER SYSTEMS AND MATERIALS USED TO HARNESS, DIRECT, CONTROL AND STORE FLUIDS

(71) Applicants: Gregory J. Hummer, Shaker Heights, OH (US); Matthew Hummer, Washington, DC (US)

(72) Inventors: Gregory J. Hummer, Shaker Heights, OH (US); Matthew Hummer, Washington, DC (US)

(*) Notice: Subject to any disclaimer, the term of this patent is extended or adjusted under 35 U.S.C. 154(b) by 206 days.

(21) Appl. No.: 15/988,608

(22) Filed: May 24, 2018

(65) Prior Publication Data

US 2018/0321214 A1    Nov. 8, 2018

Related U.S. Application Data

(63) Continuation-in-part of application No. 15/891,410, filed on Feb. 8, 2018, now Pat. No. 10,395,503, which is a continuation of application No. 15/235,981, filed on Aug. 12, 2016, now Pat. No. 9,922,525.

(60) Provisional application No. 62/511,577, filed on May 26, 2017, provisional application No. 62/297,385, (Continued)

(51) Int. Cl.
*G01N 33/18* (2006.01)
*C02F 103/42* (2006.01)
*G08B 21/08* (2006.01)
*G08B 21/12* (2006.01)

(52) U.S. Cl.
CPC ......... *G01N 33/1826* (2013.01); *G08B 21/08* (2013.01); *G08B 21/12* (2013.01); *C02F 2103/42* (2013.01)

(58) Field of Classification Search
CPC .... G08B 21/08; G08B 21/12; G01N 33/1826; C02F 2103/42
See application file for complete search history.

(56) References Cited

U.S. PATENT DOCUMENTS 7,176,793 B1   2/2007 Hummer
7,667,593 B1   2/2010 Hummer
7,911,336 B1   3/2011 Hummer
(Continued)

OTHER PUBLICATIONS

Article Application of Nanotechnology in Pesticides Removal from Aqueous Solutions—A review, T. Taghizade Firozjaee et al., Int. J. Nanosci. Nanotechnol., vol. 14, No. 1, Mar. 2018, pp. 43-56.

*Primary Examiner* — Natalie Huls
(74) *Attorney, Agent, or Firm* — Fay Sharpe LLP

(57) ABSTRACT

A monitoring system and method for any type of fluid system. Exemplary fluid systems include: sanitary and/or storm sewer systems; hydrological power generation, heating and cooling systems; energy exploration, excavation and transmission, specifically hydraulic fracturing known as "fracking". The system and method utilize chemical sensors and other detection devices, a power source and circuitry to communicate with hand-held devices and/or other local or remote data terminals. Since sewers and other water infrastructure are often used to dispose, transport, store and transform liquids or other materials in addition to human waste and/or waste fluids from other human activity, monitoring effluent and chemical composition of liquids can provide data useful for a wide range of purposes.

11 Claims, 15 Drawing Sheets

Related U.S. Application Data filed on Feb. 19, 2016, provisional application No. 62/205,012, filed on Aug. 14, 2015.

(56) References Cited

U.S. PATENT DOCUMENTS

| | | |
|---|---|---|
| D641,013 S | 7/2011 | Richardson et al. |
| 8,204,561 B2 | 6/2012 | Mongan et al. |
| 8,629,770 B2 | 1/2014 | Hummer et al. |
| 8,674,827 B2 | 3/2014 | Hummer |
| 8,930,341 B2 | 1/2015 | Amin et al. |
| 9,241,054 B1 | 1/2016 | Roberts |
| 9,400,269 B2 | 7/2016 | Kambhampati |
| 9,922,525 B2 | 3/2018 | Hummer |
| 2004/0119591 A1 | 6/2004 | Peeters |
| 2004/0197922 A1* | 10/2004 | Cooper ............... G01N 33/18 436/52 |
| 2004/0212510 A1* | 10/2004 | Aronstam ............ E21B 47/12 340/606 |
| 2005/0022581 A1* | 2/2005 | Sunshine ........... G01N 33/0073 73/31.05 |
| 2006/0289363 A1* | 12/2006 | Whitmore, Sr. ......... C02F 1/008 210/749 |
| 2008/0281534 A1* | 11/2008 | Hurley ................... F17D 5/00 702/47 |
| 2009/0123340 A1* | 5/2009 | Knudsen ............... G08B 21/12 422/105 |
| 2010/0064775 A1* | 3/2010 | Ben-Mansour ..... G01M 3/2823 73/40.5 A |
| 2011/0190939 A1* | 8/2011 | Lou ....................... F23C 99/00 700/274 |
| 2011/0283821 A1* | 11/2011 | Ober .................. G01N 33/0031 73/866.1 |
| 2014/0303757 A1* | 10/2014 | Pruchniewski ......... H04L 61/20 700/90 |
| 2014/0349707 A1 | 11/2014 | Bang |
| 2014/0377130 A1 | 12/2014 | Edwards |
| 2015/0326061 A1 | 11/2015 | Davison |
| 2015/0345688 A1* | 12/2015 | Kersey ..................... F17D 5/02 138/145 |
| 2018/0038815 A1 | 2/2018 | Gu et al. |
| 2018/0120169 A1* | 5/2018 | Jackson .............. H04L 63/0428 |

\* cited by examiner

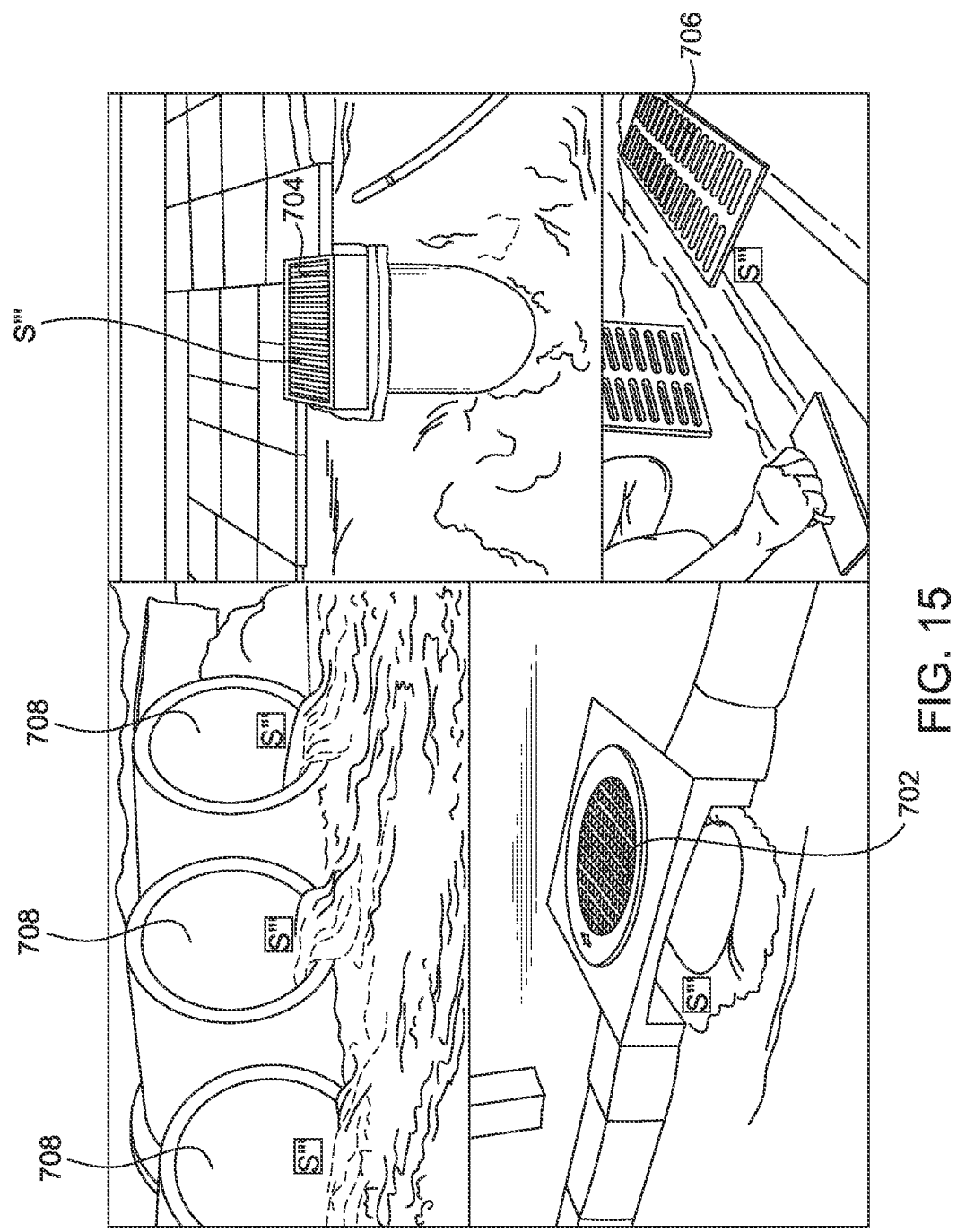

CHEMICAL SENSOR DEVICES AND METHODS FOR DETECTING CHEMICALS IN FLOW CONDUITS, POOLS AND OTHER SYSTEMS AND MATERIALS USED TO HARNESS, DIRECT, CONTROL AND STORE FLUIDS

CROSS REFERENCE TO RELATED PATENTS AND APPLICATIONS

This application claims priority to and the benefit of the filing date of U.S. Provisional Patent Application Ser. No. 62/511,577, filed May 26, 2017, and is a continuation-in-part of currently pending U.S. patent application Ser. No. 15/891, 410, filed on Feb. 8, 2018, which is a continuation of U.S. patent application Ser. No. 15/235,981, filed Aug. 12, 2016, now U.S. Pat. No. 9,922,525, issued Mar. 20, 2018, which claims the benefit of U.S. Provisional Patent Application Ser. No. 62/297,385, filed Feb. 19, 2016 and U.S. Provisional Patent Application Ser. No. 62/205,012, filed Aug. 14, 2015, which applications are hereby incorporated by reference.

FIELD

The present exemplary embodiment relates to systems and methods for detecting chemicals. It finds particular application in conjunction with systems and method for detecting chemicals in fluid, including water treatment, transmission, distribution, transformation and storage system. Such systems include but are not limited to: systems for removal of waste and/or storm water elements; power generation; irrigating agriculture; heating and cooling infrastructure, plants and equipment and energy exploration, excavation and transmission and will be described with particular reference thereto. However, it is to be appreciated that the present exemplary embodiment is also amenable to other like applications where fluid is transmitted, processed, stored, harnessed, controlled, etc.

BACKGROUND

Fluid systems are used to transport, process, store and otherwise handle a wide variety of fluids. Such fluid systems can include drinking water systems, storm and sanitary sewer systems, fracking fluid systems, etc. In many cases, the fluid systems may interconnect a large portion of the population of a given area. For example, hundreds of thousands of people may be served by a given drinking water distribution system. Likewise, these same people may send wastewater into a common sanitary sewer system. Monitoring of such fluid systems for the presence or absence of certain chemicals has heretofore been a laborious process that often includes incomplete data and lacks real-time sensing and feedback.

SUMMARY

Aspects of the present disclosure include a monitoring system for any type of fluid system. Such fluid systems can include: sanitary and/or storm sewer systems; hydrological power generation, heating and cooling systems; energy exploration, excavation and transmission systems, such as hydraulic fracturing systems known as "fracking". The monitoring system can include chemical sensors and other detection devices, a power source and circuitry to communicate with hand-held devices and/or other local or remote data terminals. Since sewers and other water infrastructure are often used to dispose, transport, store and transform liquids or other materials in addition to human waste and/or waste fluids from other human activity, monitoring effluent and chemical composition of liquids can provide data useful for a wide range of purposes.

The detection device can comprise an array of sensors and other detection devices (e.g., as noted above) that are connected to an analyzer and memory which contain algorithms, which can be downloaded from a central source, that allow the sensors and other detection devices to detect and differentiate multiple chemicals and/or gases. The sensors communicate with the CPU/memory and then report their findings via a standard wireless connection, near-field or other wireless connection (which can be encrypted). Wired transmission of data can also be utilized.

The present disclosure sets forth various detection devices placed inside or attached to or within a flow conduit, such as a sewer line, waste water line, fracking fluid line, pipes and coils, pressure fittings, reservoirs, storage tanks or any other type of physical material that harnesses or controls fluid and is otherwise positioned to sample effluent or other desired fluid streams. The detection devices can also be designed to bob or wade in standing fluids such as reservoirs, pools or tanks. The detection devices can be strategically placed at nodes of systems whereby fluid tends to flow, stagnate or coagulate, and can be configured to work together to determine a location or a most likely location of an inflow of a detected chemical, or otherwise approximate a location of an inflow of a particular chemical.

Aspects of the present disclosure can provide operators of assets including capital plant and equipment, researchers and law enforcement agencies real-time data on the presence and/or concentration of certain monitored chemical compounds within the sampled fluid stream or streams. The information can be used to detect certain chemicals associated with, for example, bomb-making, such that law enforcement can be alerted to potential threats with sufficient time to investigate the source of the identified chemical (s) and potentially neutralize the threat. In addition, certain compounds associated with illicit drug manufacture and/or use can be detected thereby potentially giving law enforcement sufficient evidence to pursue an investigation that would otherwise not be able to proceed. Other examples include instances where the chemical composition of liquid mixtures must be known for purposes associated with operational effectiveness, regulatory compliance, sanitation or avoiding harm to the environment and/or other living organisms. Such applications include, but are not limited to: methods for extracting, capturing and transmitting sources of energy including natural gas and oil; controlling temperatures of plant and equipment including energy/computing processors, generators, transistors and/or storage tanks and irrigating plants, other processing plants and factories and physical infrastructure.

In accordance with one aspect, a monitoring device is disclosed for monitoring a flow conduit or pool for the presence of one or more chemicals or concentration level of one or more chemicals in a fluid flowing through the conduit or within the pool. The monitoring device includes at least one sensor including a detector component operative to generate data in response to the presence of one or more chemicals, communication circuitry and a power source operatively coupled to the detector component and the communication circuitry for supplying power thereto, the communication circuitry configured to transmit data generated by the detector component corresponding to the presence or absence of one or more chemicals to an associated receiver.

The flow conduit can include at least one of a sewer pipe, channel, trough, open or closed fluid transmission line, heating and cooling coils or other physical material that harnesses, directs or controls fluid. The pool can include at least one of a reservoir, holding area, storage tank, volume drum, liquid bunker, pit, pond, hole or bowl. The device can be fixed to an interior surface of the flow conduit, or the device can be portable.

In some embodiments, the device can be mobile within the conduit or the pool. The device can have a density equal to or less than a density of the fluid. The device can be tethered to the flow conduit or pool such that the device has a limited range of motion therein.

The power source can include an antenna configured to receive energy wirelessly and supply the received energy to at least one of the detector component or the communication circuitry.

In accordance with another aspect, a method of monitoring a flow conduit or pool for the presence of or concentration level of one or more chemicals, the method comprises providing a plurality of sensors, each sensor including a detector component operative to generate data in response to the presence of one or more chemicals, communication circuitry and a power source operatively coupled to the detector component and the communication circuitry for supplying power thereto, the communication circuitry configured to transmit data generated by the detector component corresponding to the presence or absence of one or more chemicals to an associated receiver, associating each sensor with a location within the flow conduit or pool to be monitored, monitoring each location with its associated sensor over a period of time, and transmitting data generated by each sensors to a receiver.

Each sensor can be configured to sense a concentration of the one or more chemicals. The method can further include approximating a location of ingress of the one or more chemicals into the flow conduit (or network of same) based at least in part on data generated by two or more sensors. The method can also include comparing the location and detected concentration of one or more chemicals of the two or more sensors to approximate the location of ingress of the one or more chemicals.

In some embodiments, the sensors can be configured to sense a concentration of the one or more chemicals, and generate data indicative of the sensed concentration. The sensors can be configured to periodically report a sensed concentration over a period of time. The method can further include comparing the sensed concentration to a threshold concentration, and generating an alert if the sensed concentration exceeds the threshold concentration. The method can also include providing a power source including an antenna configured to receive energy wirelessly and supply the received energy to at least one of the detector component or the communication circuitry.

BRIEF DESCRIPTION OF THE DRAWINGS

FIG. 15 illustrates perspective views of intake and discharge components in accordance with the present disclosure.

DETAILED DESCRIPTION

Figure 1:
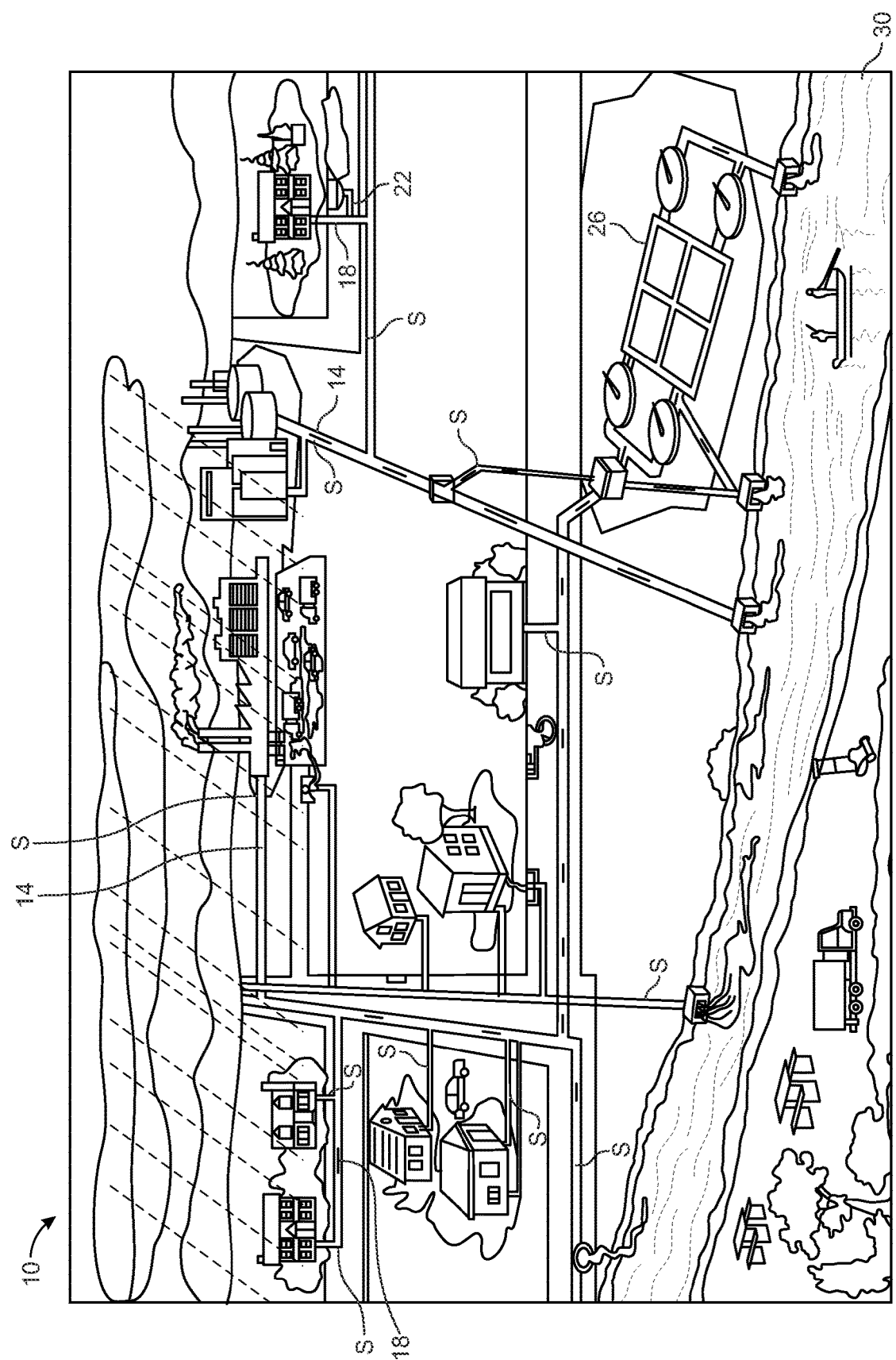
FIG. 1 is an overview of an exemplary fluid conduit network in the form of split and combined sewer systems including sensors in accordance with the present disclosure.

Turning to the FIGURES, FIG. 1 illustrates an exemplary network of flow conduits 10 for water use and treatment. FIG. 1 also shows exemplary locations where sensors in accordance with the present disclosure can be placed and used to detect various levels of unwanted chemicals in fluids or water at the various stages of the water use and treatment process. The network of flow conduits 10 is exemplary in nature, such networks being well-known. Aspects of the present disclosure can be implemented in virtually any setting where monitoring a flow of fluid for particular chemicals is desired. This includes potable water delivery systems, wastewater treatment systems, storm water, etc.

In the exemplary network 10, both a split sewer system and a combined sewer system are in use. A split sewer system routes wastewater and storm water through separate conduits, while a combined sewer system routes wastewater and storm water through common conduits.

Water use can begin with industrial wastewater 14 and residential wastewater 18. It can also begin with industrial storm water and residential storm water 22. In the split sewer system, storm water from residential and industrial sources are combined into main branches of the storm sewer and wastewater from residential and industrial sources are combined into main branches of the sanitary sewer. Industrial wastewater and residential wastewater are both sent to wastewater treatment plant 26 for processing and then released into natural water sources 30. Storm water from industrial and residential sources flow directly through storm water point sources into natural water sources 30 in the split sewer system, or overflows into natural water sources via the wastewater treatment plant in the combined sewer system.

Sensors S can be placed in strategic locations throughout the network 10 (e.g., in the invert of flow conduits from all sources). They can also be placed on other associated water infrastructure including sewer grates, drains, channels and gutters or open flows. After the water flows through the sanitary and storm sewer pipe system, sensors can be placed throughout sewage treatment plants and drinking water treatment plants. FIG. 1 illustrates several exemplary locations for the sensors S, but it should be appreciated that sensors can also be placed in other locations.

Figure 2:
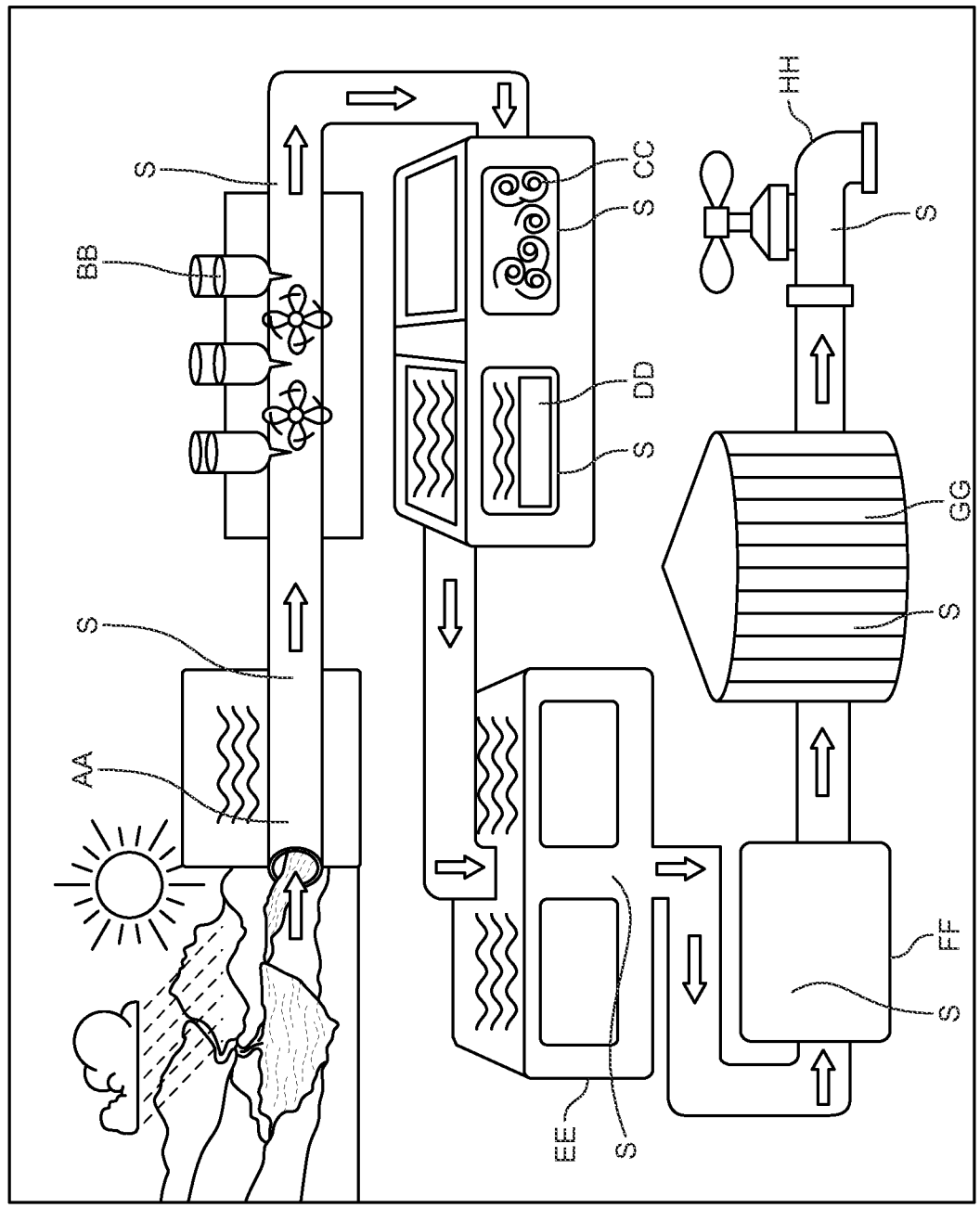
FIG. 2 is a schematic diagram illustrating an exemplary water treatment plant in accordance with the present disclosure.

FIG. 2 illustrates an exemplary embodiment wherein sensors S are deployed at water treatment plants to monitor levels of chemicals present in water. Sensors S can be placed in the invert of water intake flow conduits or pipes AA. Sensors can also be placed in the invert of pipes and infrastructure used for mixing chemical additions (chlorine, lime and alum) BB. Sensors S can also deployed in bobbing mechanisms, for example, in following stages involving coagulation CC sedimentation DD, filtration EE, disinfect FF and storage GG. Sensors S can also be placed in the invert of pipe in distribution HH; such sensors can provide data to consumers so they can understand the chemical composition of the water they are consuming.

Figure 3:
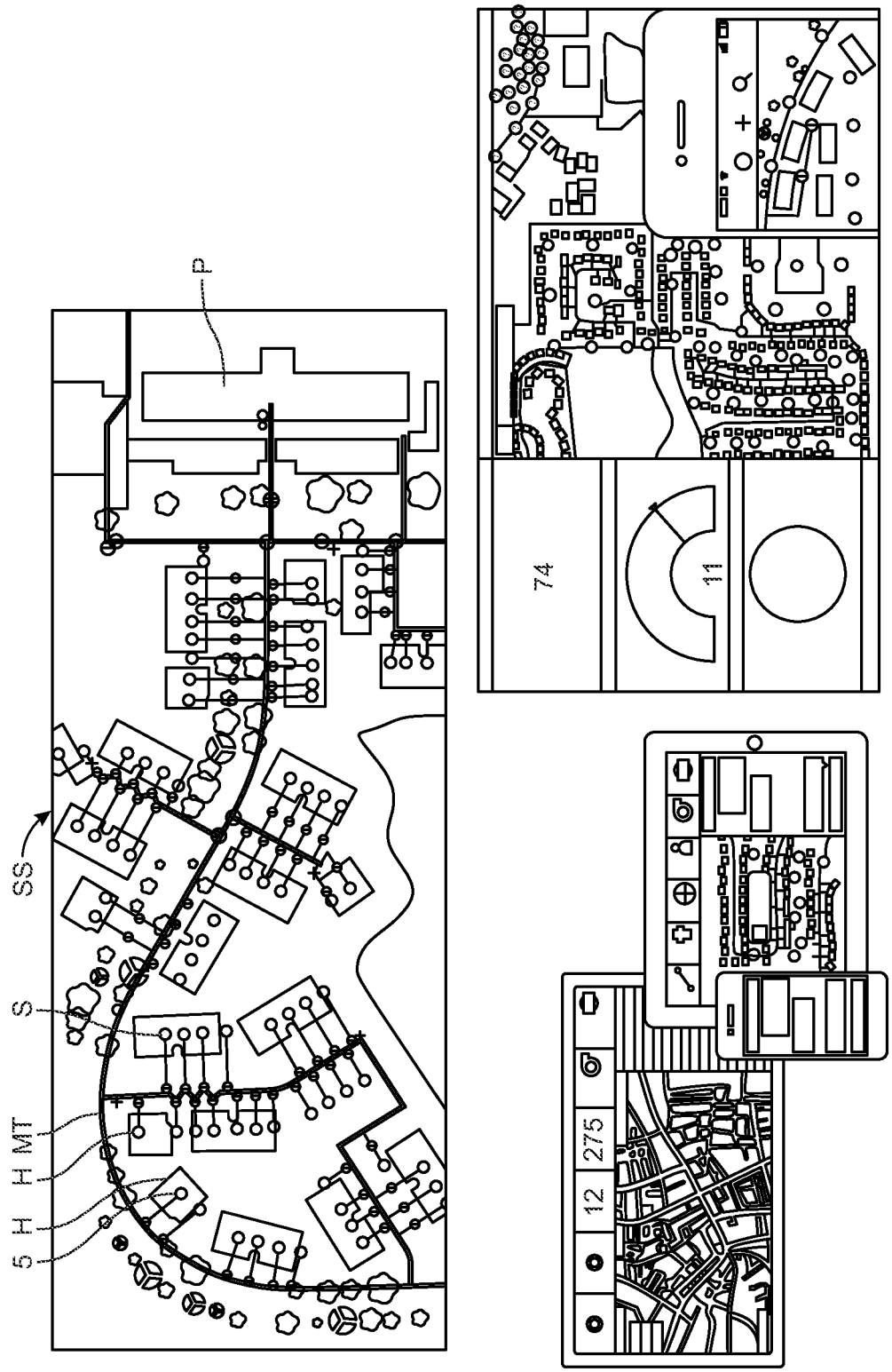
FIG. 3 is a schematic diagram of another exemplary sewer system including a plurality of sensors S in accordance with the present disclosure.

FIG. 3 illustrates an exemplary sewer system SS including a plurality of sensors S in accordance with the present disclosure. The sewer system SS generally comprises a main trunk line MT leading to a sewage treatment plant P. Individual houses H, buildings, or other end user structures are connect to the sewage treatment plant via a lateral line, branch line, trunk line, staging pools or combination thereof. Although the terminology used for describing sewer components may vary, for the purposes of the present disclosure it only need be understood that one or more flow conduits or pools connect each point source of fluid to the treatment plant. It should be appreciated that aspects of the present disclosure are not limited to any particular sewer arrangement. It should also be appreciated that any number of sensors S with varying designs can be utilized depending on the particular application. In addition, the sensors S can be configured to work together or work individually to detect the presence of chemicals/gases the concentration levels of chemicals/gases as well as other factors that provide operational support of sensor applications including but not limited to: temperature, humidity and liquid flow rate as will be described.

Figure 4:
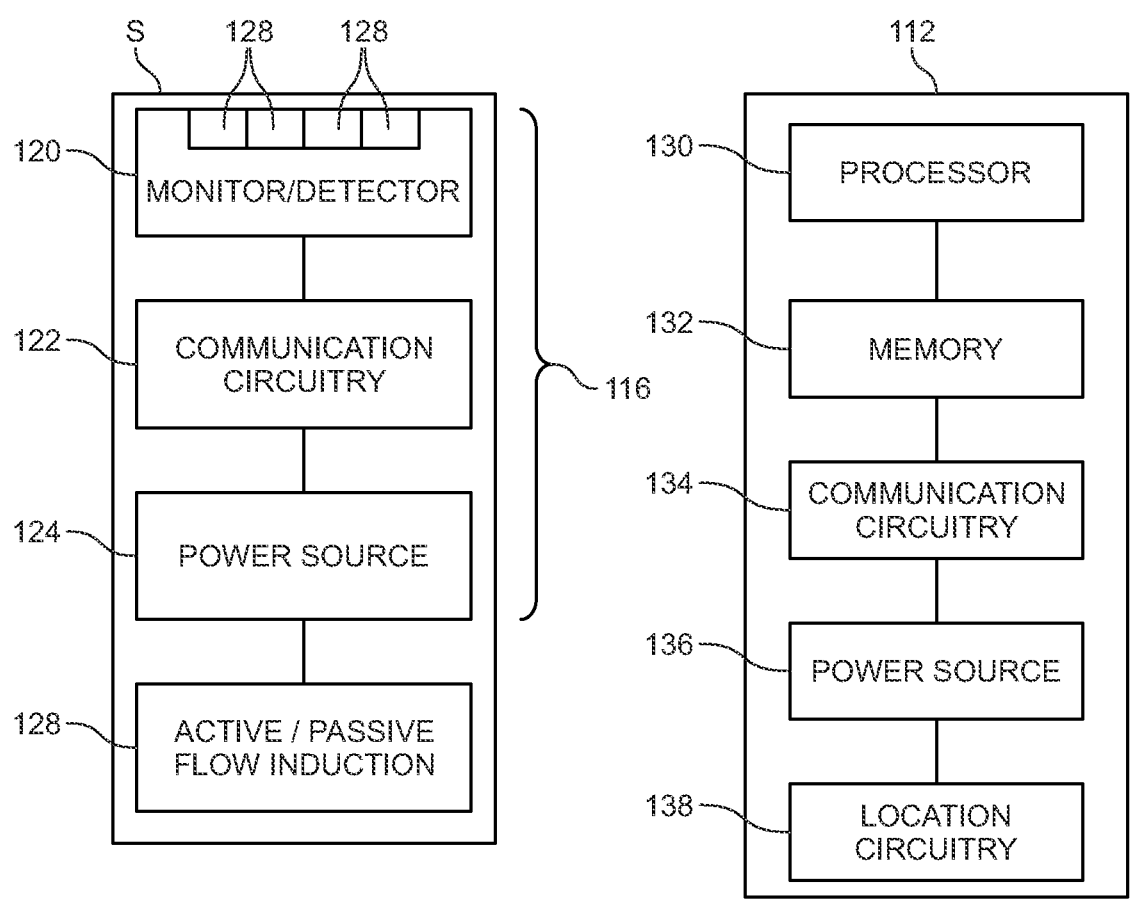
FIG. 4 is a block diagram of an exemplary sensor and receiver in accordance with the present disclosure.

With further reference to FIG. 4, the sensor S includes communication circuitry 122 and a power source 124. The communication circuitry 122, in one embodiment, includes at least one of a near field communication device, Bluetooth communication device, WIFI communication device, or any other suitable communication circuitry for establishing communications with a remote processing device 112. The power source 124 can be a power supply such as a battery (lithium or other including solar cell). In other embodiments, the power source 24 can be an antenna configured to receive energy wirelessly and supply the received energy to one or both of the monitor/detector component 120 and/or communication circuitry 122 such that no onboard battery is required for operation of the monitor system 116.

An active or passive flow induction device 126 can be provided for ensuring adequate and or continuous flow of fluid to the monitor/detector component 20. Such devices can include funnels, channels flow paths, fans, pumps, micropumps, louvers, vents etc. An active induction device can be separately replaceable within the system and can include its own power supply. Alternatively, an active induction device can be configured to receive power from power supply 124.

It should be appreciated that the monitor/detector component 120 can comprise a plurality of sensor elements 128.

The sensor elements 128 can be individually replaceable or can be replaced as a unit. Replacement of the sensors may be necessary due to sensor degradation. In other situations, a user may wish to detect certain chemicals and will choose which sensors to install in the system. In one embodiment, the entire sensor S is replaceable as a unit.

The sensor elements 128 may detect any chemical, such as the chemicals referred to above.

It will be appreciated that the sensor S is configured to communicate with the remote processing device 112. That is, the sensor S collects data and transmits or otherwise shares the collected data with the remote processing device 112 for processing. The remote processing device 112 of the illustrated embodiment includes a processor 130, a memory 132, a communication circuitry 134, a power source 136 and temperature, humidity and location circuitry (e.g., GPS, and/or inertia/acceleration sensors). It will be appreciated that the remote processing device 112 can include a wide variety of additional components as is conventional. Such additional components can include a display device, input device, various sensors, various antennas, etc. In some examples, the processor and memory can be onboard the sensor S.

Data collected by the monitor/detector component 120 is transmitted via communication circuitry 122 to communication circuitry 134 of the remote processing device 112. Other data, such as sensor state, status, performance data, and the like can also be transmitted to the remote processing device 112. Any suitable manner of transmitting the data from the sensor S to the remote processing device 112 can be employed.

The data collected and transmitted by the sensor S is then processed by the remote processing device 12 to detect one or more chemicals in accordance with one or more methods, for example the methods set forth in U.S. Pat. No. 8,629,770 to Hummer et al. and U.S. Pat. No. 7,176,793 to Hummer, which are both hereby incorporated herein by reference in their entireties. To this end, suitable software for analyzing the data is stored in memory 132 of the remote processing device 112. Other detection and/or analyzing methods and techniques may also be used in conjunction with aspects of the present disclosure. It should be appreciated that the sensor S and remote processing device 112, although shown as separate components, can be provided in a common housing if desired. In such case, the remote processing device 112 could then transmit an alert, alarm or other signal indicative of a detected chemical and/or concentration thereof.

In one embodiment, the software stored in memory 132 can be in the form of an application, or "app," that is downloaded from an app store or the like. The app can be provided with various "signatures" of chemicals. The signatures can be compared to the data to determine whether the chemical signature was detected by the sensor system S. The app can be configured to be automatically updated with new signatures as the need to detect particular chemicals arise. That is, it is possible to provide new and/or additional chemical signatures for the app to check against the data to detect specific chemicals.

The app can further include features such as adjustable thresholds. For example, for some chemicals that are routinely present in certain amounts and/or not generally considered dangerous or problematic below certain levels, the application can be configured to detect or trigger an alarm when a threshold amount is met or exceeded. For some chemicals which are considered dangerous or problematic in any amount, the thresholds would not generally be adjustable.

The app can be further configured to, once a chemical is detected, share the detection information. For example, the application can be configured to use the communication circuitry 134 to broadcast an alert (or generate a notification) via any suitable communications network (e.g., WIFI, NFC, Bluetooth, cell, etc.). The alert may be directly sent to other, for example, personal communication device of physical asset operator, or may be sent to the cloud, a server (or through a network) and then on to devices within a range of a given location or assigned a specific task pertaining to chemical monitoring.

Figure 5:
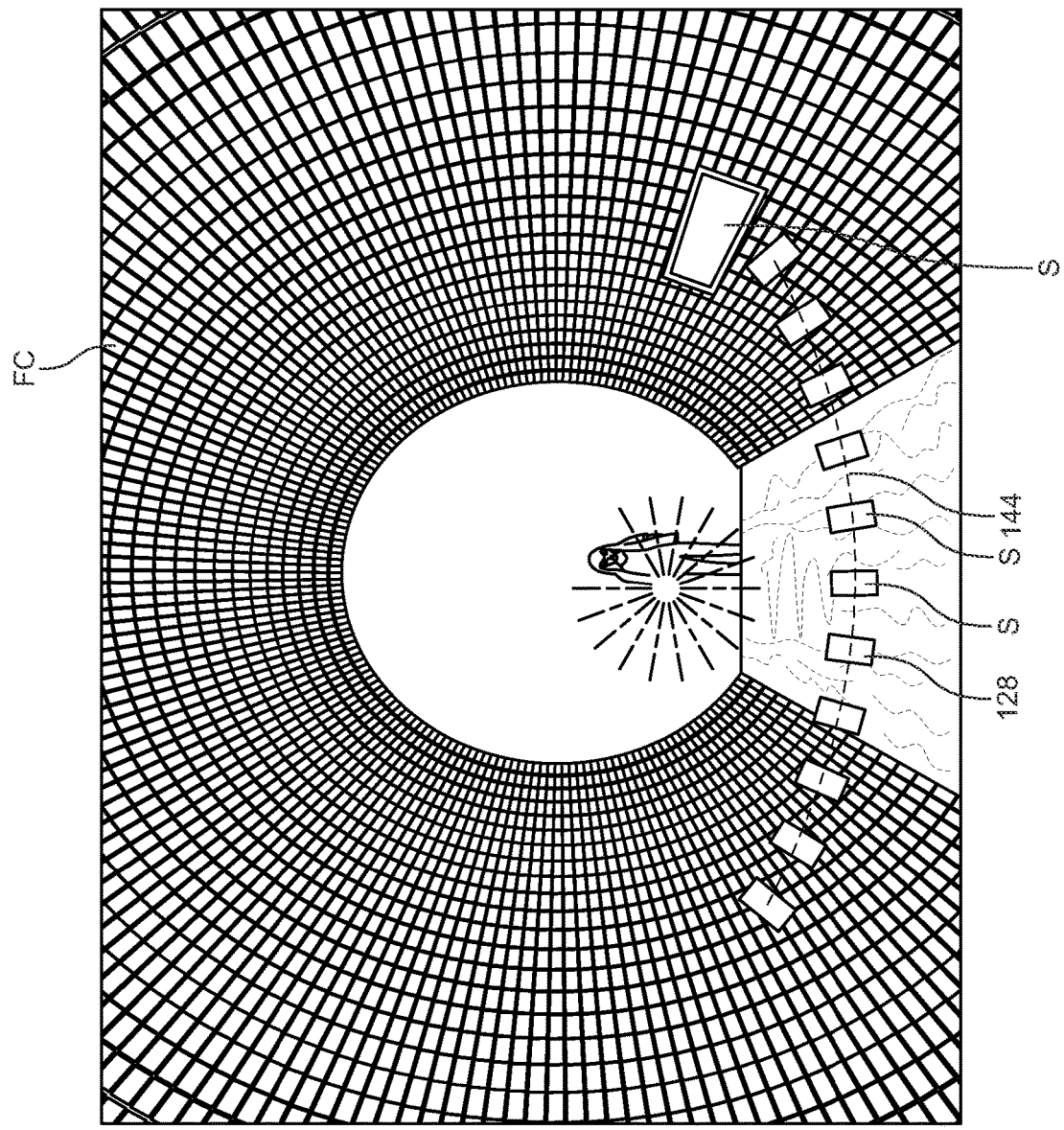
FIG. 5 illustrates an exemplary sensor installed in a flow conduit in accordance with the present disclosure.

FIG. 5 illustrates an exemplary placement of a sensor S with multiple sensor elements S in the invert of flow conduit FC, pipe, storm sewer or other flow channel. In this example, the sensor elements S are arranged along the invert of the flow conduit FC up to the historical high waterline ensuring the sensor elements S encounter all water flow. Flow concentrators can also be used to funnel water towards the sensor elements S strategically placed where water flow is greatest. In this embodiment, multiple sensor elements S are arranged perpendicular to the flow direction. The sensor elements S are mounted to a strap or ribbon 144, which in turn is secured along at least a portion of its length across the flow direction to the flow conduit FC.

Figure 6:
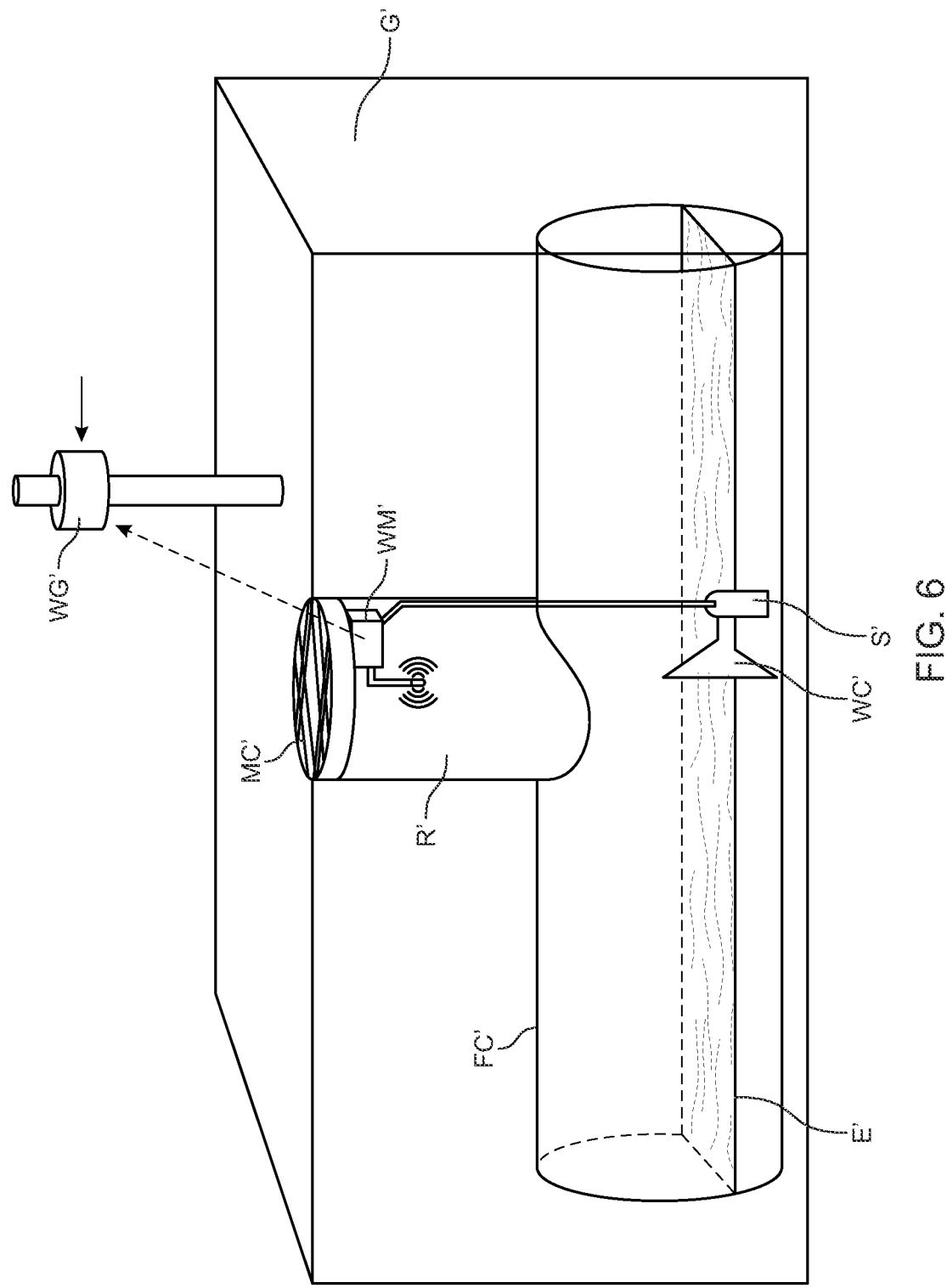
FIG. 6 illustrates another exemplary sensor installed in a flow conduit in accordance with the present disclosure.

In FIG. 6, an exemplary sewer pipe or flow conduit FC' is illustrated buried in the ground G' in a typical fashion. A riser pipe R' (e.g., a manhole) provides access to the flow conduit FC' from grade level. Effluent E' is shown flowing in the bottom portion of the flow conduit FC'. Wireless gateways WG' can also be placed strategically above ground to ensure strong communication with wireless module WM' placed on the inside of a manhole cover MC' or other suitable places within storm/waste water infrastructure. FIG. 6 also shows other methods of deploying sensors in the invert of flow conduits including a sensor S' tethered to the wired/wireless module or other infrastructure components. A water concentrator WC' in the form of a funnel can be used to force/direct water flow to the sensor S' within the flow conduit FC'. Other water concentrators can be employed, including active water concentrators that actively direct flow to the sensor S'.

The sensor S' is illustrated secured to the flow conduit FC. The sensor S' can include the components of sensor S described above. The sensor S' can be secured within the flow conduit FC' in a position that ensures at least a portion thereof is submerged in the effluent E'. Sensor elements on this portion of the sensor S' can be used to detect certain volatile chemicals that may be present in the air space of the flow conduit FC'. It should be appreciated that any suitable fasteners, such as rivets, screws etc., or adhesives, can be used to maintain the sensor S' in position.

In an alternative embodiment, the sensor S' can be configured to extend completely around the inside circumference of the pipe. In such an embodiment, a carrier or mounting structure supporting the sensor S' can be expanded by a screw mechanism to seat securely inside of a wide variety of pipe diameters.

In still another embodiment, a fitting can be provided with a port for receiving a sensor, or otherwise provided with structure to support the sensor about the circumference of the flow conduit. For example, the fitting can be a pipe union, elbow or valve body, for example. In other embodiments, the sensor may be integrally formed with the fitting.

It will be appreciated that the sensor S' can include various structures for ensuring adequate flow across sensor elements. These structures can include channels for funneling fluid or air to the sensor elements. It should also be appreciated that embodiments can include a flow sensor and/or pH sensor and/or temperature sensor and/or humidity sensor.

Figure 7:
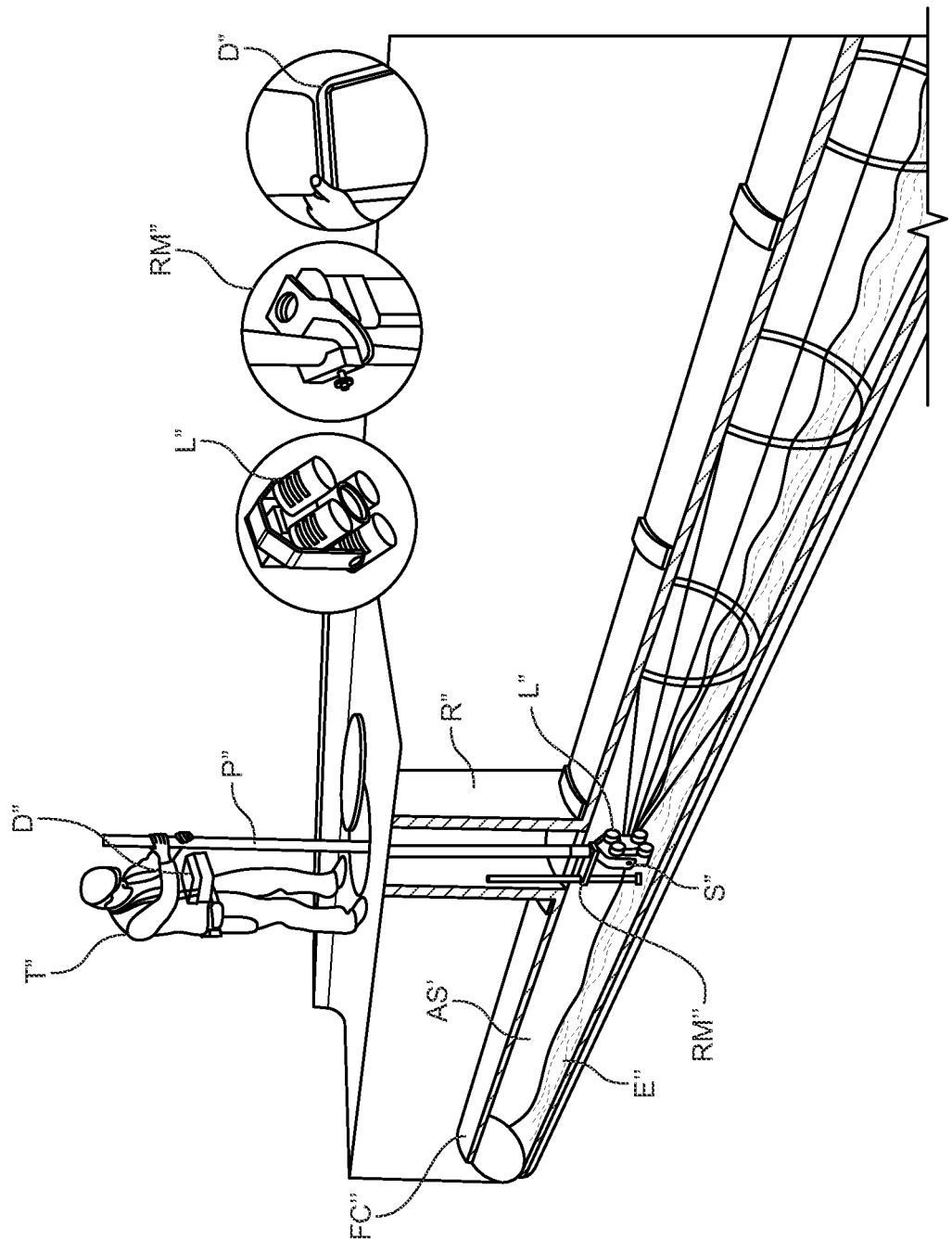
FIG. 7 illustrates an exemplary portable sensor being used to sample fluid in a flow conduit in accordance with the present disclosure.

FIG. 7 illustrates a portable and/or handheld sensor S". Sensor S" is configured to be deployed by a technician T" to sample selected flow conduits or portions thereof, as opposed to fixed sensor S' which typically only samples a single location once mounted. Sensor S" can be provided on a pole P" or other elongate member and inserted in a flow conduit FC" via a riser pipe R" as shown, or via any other suitable access point, to contact effluent E" and/or air space AS" within the flow conduit FC". The portable analyzer S" also can be equipped with lighting L", a rotation mechanism RM" to optimize sampling and an electronic display D" to view the results of chemical analyzer (CC).

Figure 8:
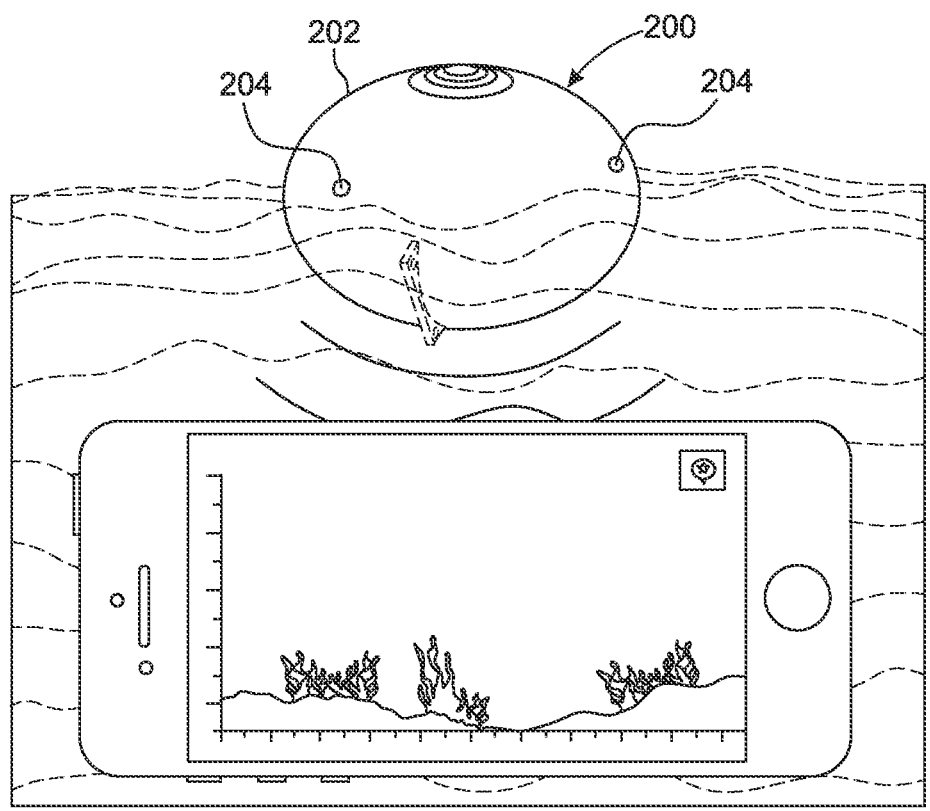
FIG. 8 is a schematic diagram of an exemplary sensor pod floating in fluid in accordance with the present disclosure.

FIG. 8 illustrates another exemplary embodiment of the present disclosure including a self-contained pod 200 containing the sensor technology described above. The pod 200 can be designed to be deployed at a first location and travel within a sewer system or other conduit to a second location while monitoring for chemicals during transit. The pod 200 has a floating mechanism 202 (e.g., spherical shell) to keep it near a surface of the fluid or, alternatively, at the level most optimal for sampling and detecting chemicals. To this end, the density of the pod 200 can be selected to be equal to or less than the density of the fluid to be sampled. The pod 200 also has a mechanism for intake/sampling of water for chemical analysis (e.g., ports 204). Built into the pod 200 can be location tracking technology, such as GPS, and other types of flow, water pressure and temperature sensors. To this end, location circuitry 138 shown in FIG. 4 can be particularly useful for determining more precise location information when a given chemical is detected. This embodiment connects wirelessly to nearby or remote data terminal showing its location along with chemical analysis data. The nearby or remote data terminal also shows all of the other pods' location and chemical analysis.

Figure 9:
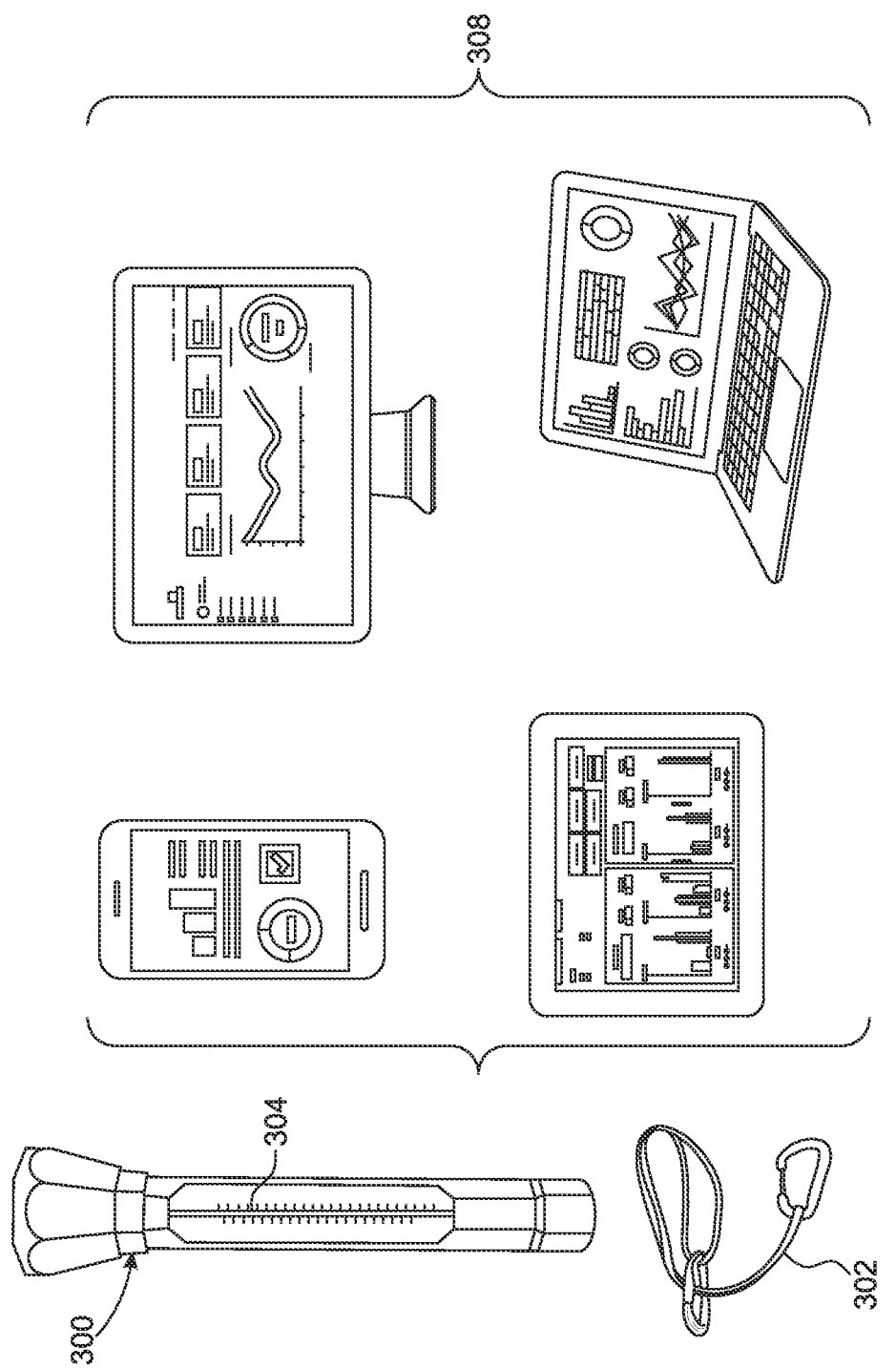
FIG. 9 is a schematic diagram of another exemplary sensor pod, tether, and remote displays in accordance with the present disclosure.

FIG. 9 shows another exemplary pod 300 in accordance with the present disclosure. In this embodiment, the pod 300 can either be free floating or tethered to a specific location using a coiled tethered connection line 302, or the like. The coiled tethered connection line 302 provides bobbing flexibility and movement within a refined area. This design also features a larger surface area (e.g., extending vertically below the surface a longer distance than pod 200) for chemical detection and can be deployed in deeper water. It also has a built-in display 304 for immediate reading of chemical analysis, location, water flow, water temperature and other factors. Like other embodiments, this example also connects and transmits data to remote displays 308 for further analysis that incorporates data from other chemical sensors deployed throughout networks and systems.

It will now be appreciated in the sensors of the present disclosure can be used to identify not only certain chemicals within a sewer, transmission line or other network of conduits and pools, but also can provide location information helpful for determining an approximate location of the point of entry of the chemical into the system or network that harnesses or controls fluid. In a sewer system having a large number of sensors deployed throughout (and particularly at intersections of pipes), the data from each sensor can be used to make inferences about where a given chemical is entering the system. With this information being provided in real-time or close to real-time law enforcement personnel, physical asset operators and maintenance providers and researchers can take appropriate action related to their associated responsibilities.

In a simplified example, a system having a sensor at the intersection of each branch line and a single trunk line may have a number of the sensors report the present of a chemical in various concentrations. The sensor with the largest concentration of the detected chemical may be most likely associated with the branch line in which the chemical is entering the trunk line. Of course, additional sensors upstream of the sensors at the branch/trunk intersection can provide more precise data. An analytical process can be employed to utilize the the concentration data and location data to estimate a most likely region for the ingress of the detected chemical.

Figure 10:
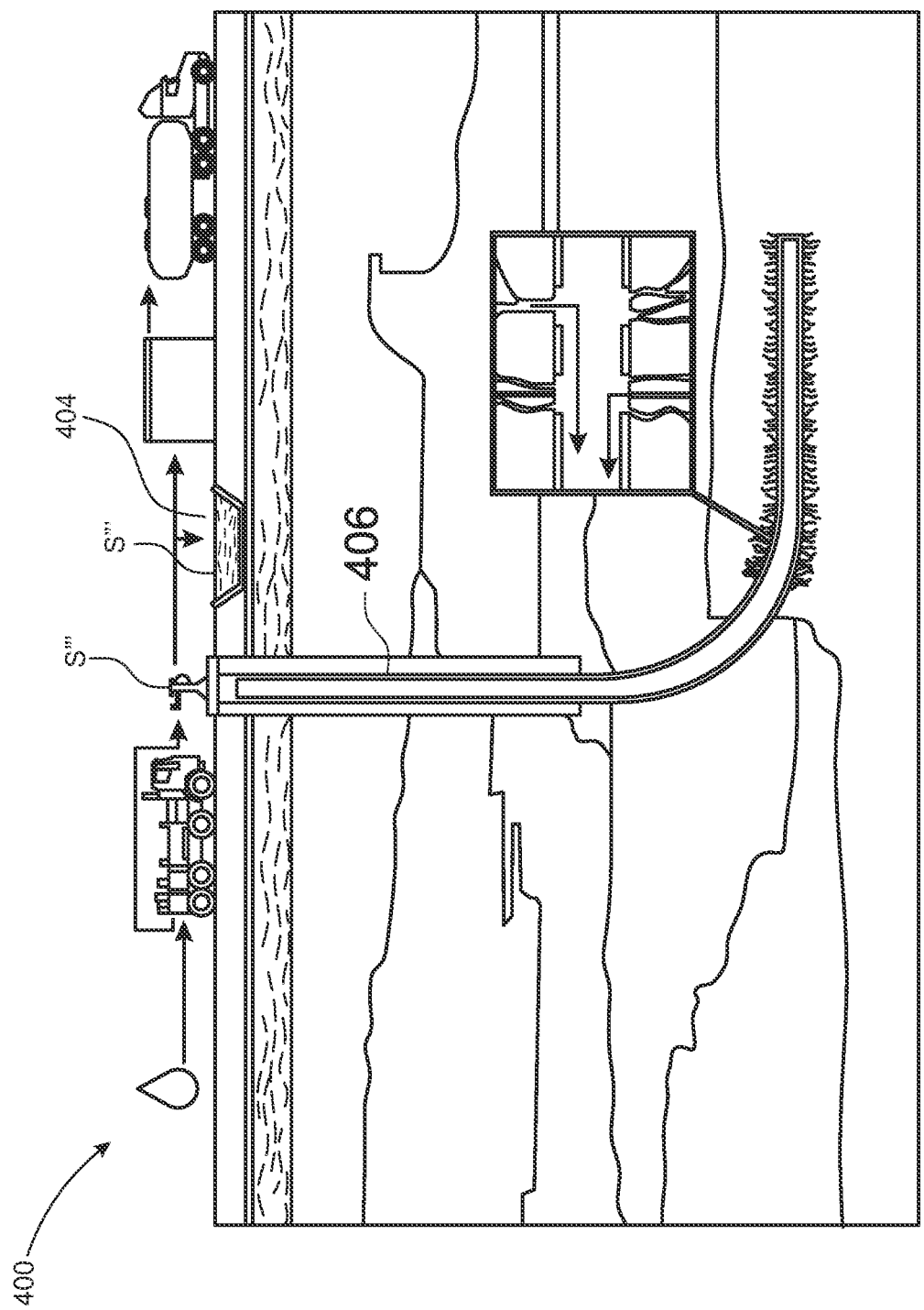
FIG. 10 is an overview of a hydraulic fracking operation.

FIG. 10 illustrates aspects of the disclosure applied in an alternative fluid system relating to energy excavation and, specifically, hydraulic fracturing ("fracking") whereby rock is fractured by a pressurized liquid that creates cracks that allow natural gas, petroleum and brine to be captured for use. A key component of fracking is having a precise understanding of the chemical composition of the fracking fluid, which is injected into the wellbore to create cracks in the deep-rock formations through which the natural gas, petroleum and brine flow. The fracking fluid can contain high levels of toxic and heavy metals in its flowback form, including barium and sulfate among other industrial chemicals (sodium, magnesium, iron, barium, strontium, manganese, methanol, chloride, sulfate among other substances); toxic hydrocarbons (benzene, toluene, ethylbenzene and xyle) and even radioactive materials (radium). The Environmental Protection Agency (EPA) currently allows a maximum of 5 picocuries of radium per liter of drinking water. Produced fracking water has been found to contain radium levels as high as 9,000 picocuries per liter, which is substantially above the EPA limit.

Figure 11:
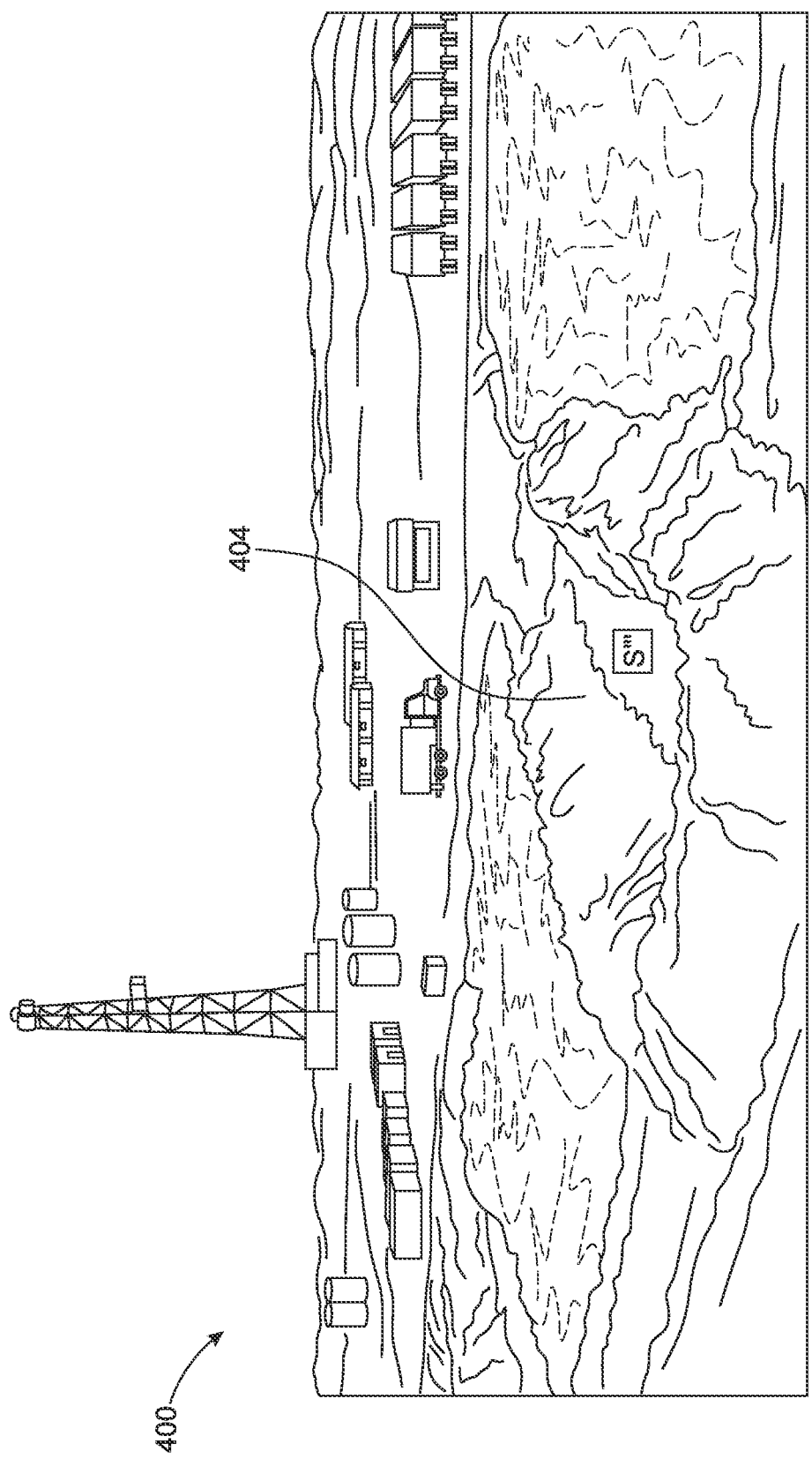
FIG. 11 is a perspective view of the hydraulic fracking operation of FIG. 10.

FIGS. 10 and 11 show an exemplary hydraulic fracturing operation 400. Fracking pits 404 where fracking fluid and flowback wastewaters are stored can be outfitted with sensors S''' in accordance with the present disclosure to monitor the fracking fluid within one or more of the fracking ponds 404. Additional sensors S''' can be provided elsewhere in the operation, such as within the well 406, for monitoring the fracking fluid at other locations. The sensors S''' provide real-time chemical detection of unwanted industrial chemicals, hydrocarbons and/or radioactive material. Detection devices can also be engineered to withstand high pressure and deployed in the invert of low pressure pipes, hoses and other flow conduits as well as high pressure pipes, hoses and other flow conduits (BB). The devices can also be deployed inside the well for detection of unwanted chemicals.

Figure 12:
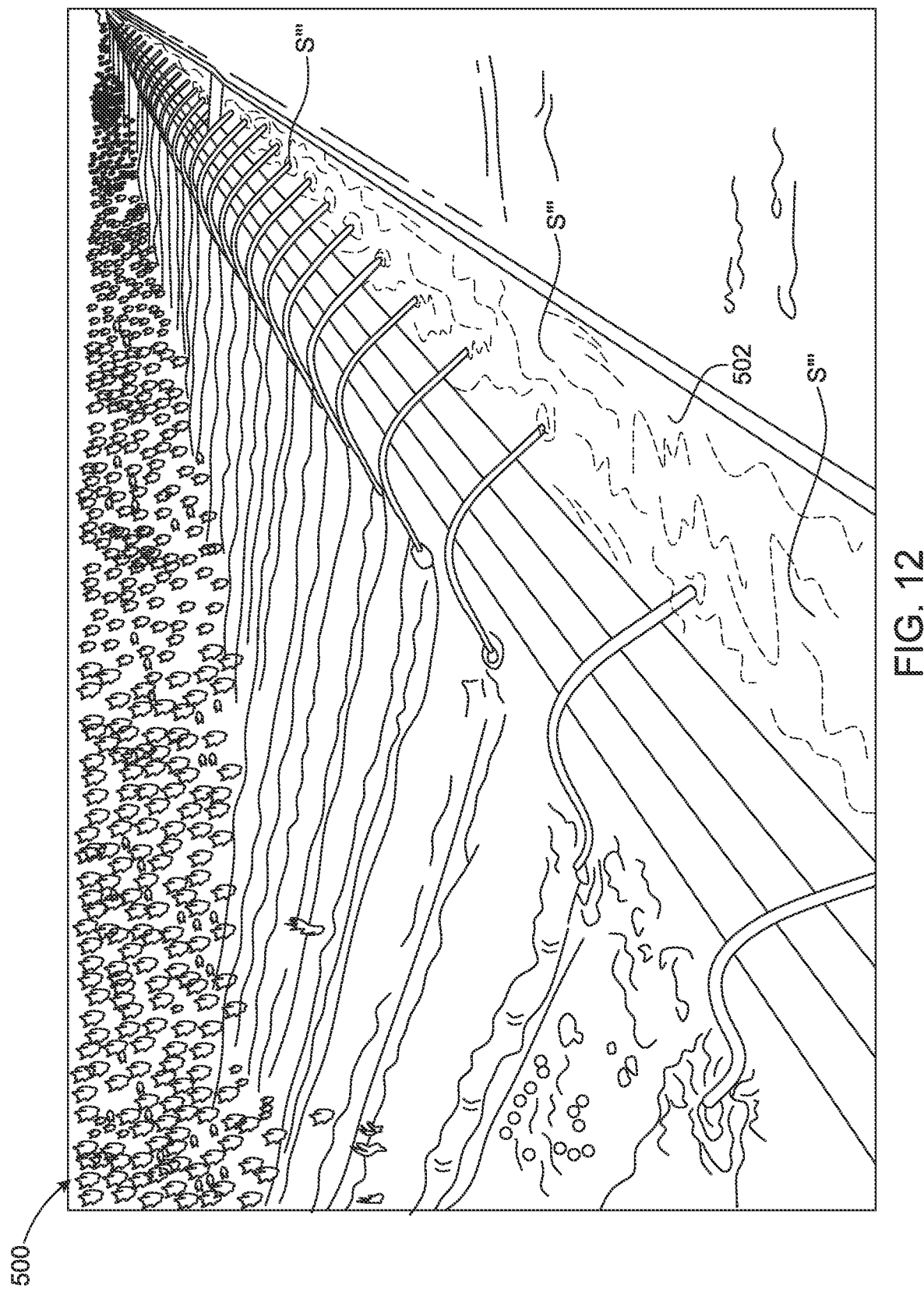
FIG. 12 is a perspective view of irrigation infrastructure in accordance with the present disclosure.

FIG. 12 illustrates still another embodiment of the present disclosure wherein sensors S''' are utilized within a crop irrigation infrastructure 500. The devices are deployed throughout the irrigation infrastructure 500 to detect levels of pesticides and other unwanted chemicals including those associated with pathogens and foodborne illness. In various examples, the sensors S''' can be placed either at the bottom of an irrigation channel (502) in accordance with the configurations shown and describe in any of FIG. 5, 8 or 9, for example.

Figure 13:
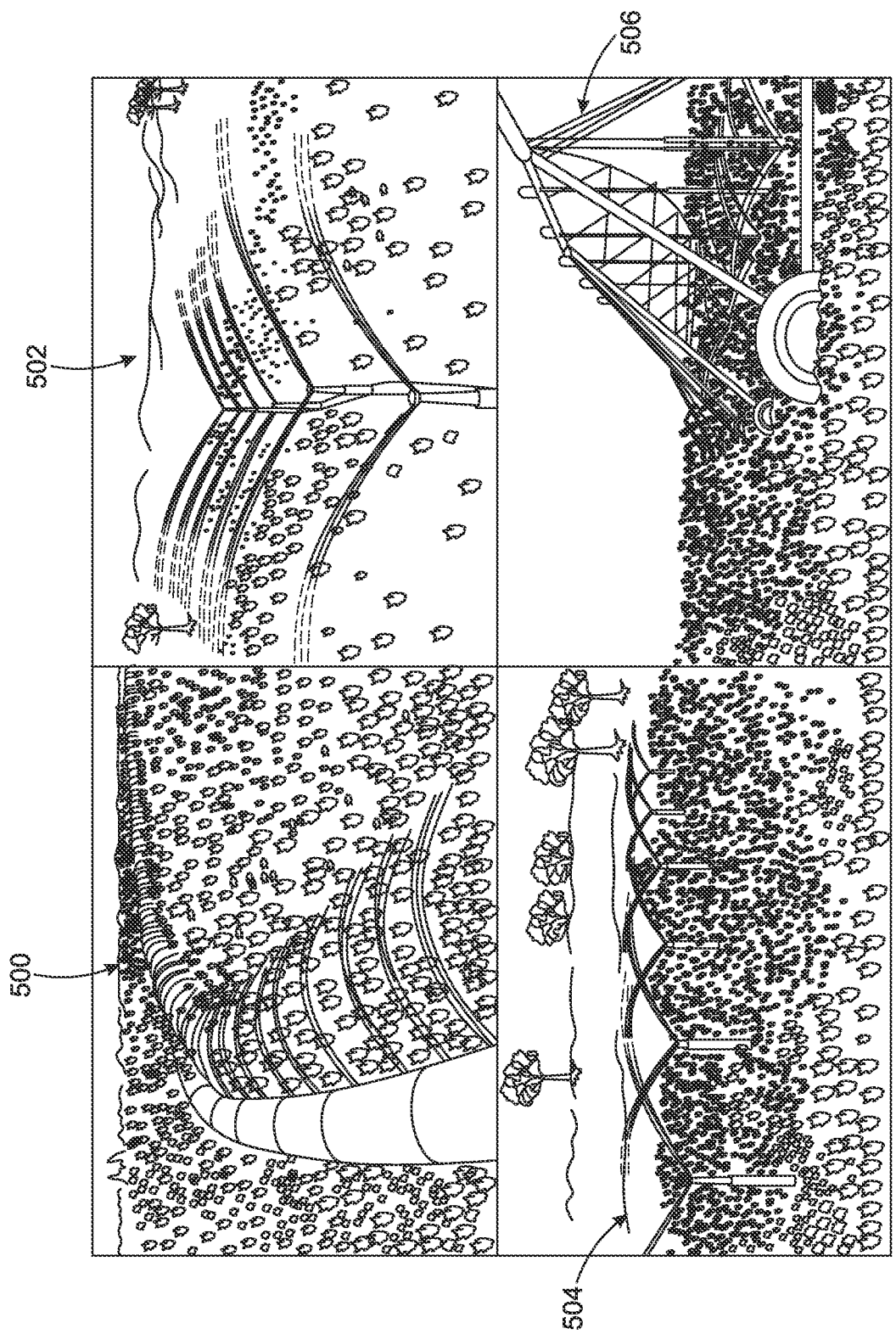
FIG. 13 illustrates additional irrigation infrastructure in accordance with the present disclosure.

FIG. 13 shows additional types of irrigation infrastructure 500, 502, 504 and 506 with which the sensors of the present disclosure can be associated for analysis of chemical composition, notably pesticides.

Figure 14:
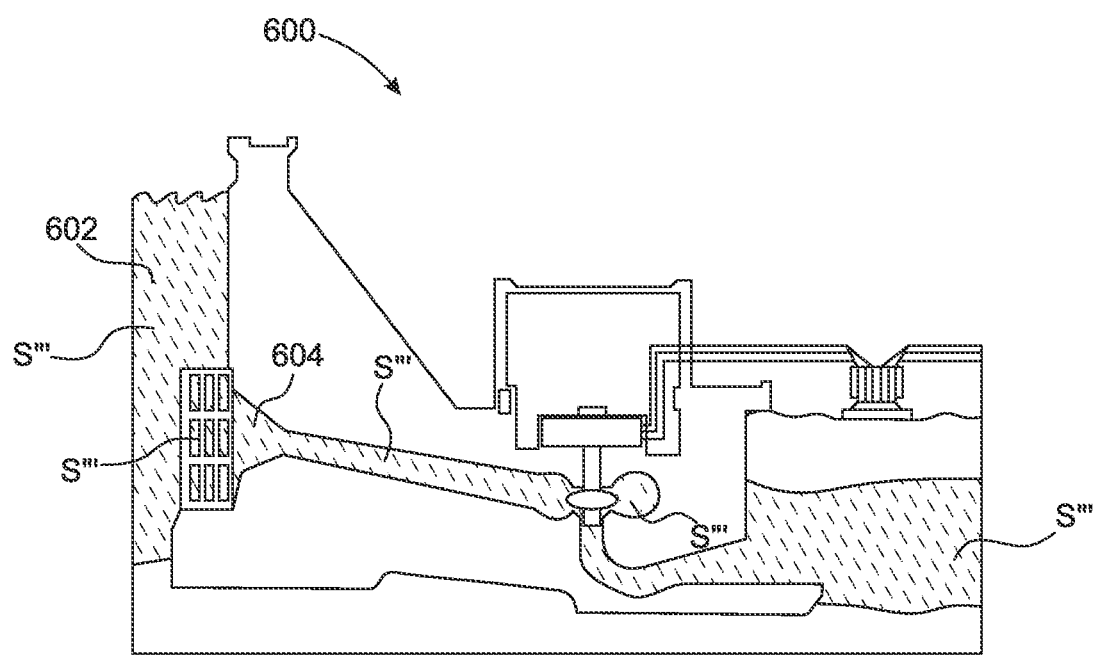
FIG. 14 is a schematic illustration of a hydroelectric generation facility in accordance with the present disclosure.

FIG. 14 illustrates yet another embodiment of the present disclosure, wherein sensors S''' are deployed in a system 600 for generating hydroelectricity. It should be appreciated that the exemplary sensors of FIGS. 5, 8 and 9 can be deployed in a reservoir 602 of the system 600, or in an intake 604, penstock 606, turbine 608 and/or discharge 610 to water source (river, steam, pond, pool or ocean).

FIG. 15 shows additional locations for sensor S''' integration in water intake/discharge infrastructure including an open storm drain 702, grated or covered storm drain 704 and grated storm channels 706 or other covered or semi-covered flow conduits, and storm sewer discharge pipes 708.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A monitoring device for monitoring a flow conduit or pool for the presence of one or more chemicals or concentration level of one or more chemicals in a fluid flowing through the conduit or within the pool, the monitoring device including at least one sensor including a detector component operative to generate data in response to the presence of one or more chemicals, a flow induction device for directing substance to the detector component, communication circuitry and a power source operatively coupled to the detector component and the communication circuitry for supplying power thereto, the communication circuitry configured to transmit data generated by the detector component corresponding to the presence or absence of one or more chemicals to an associated receiver, wherein the sensor further determines a location of the sensor, the communication circuitry configured to transmit the location to the associated receiver, wherein at least one of the detector component, communication circuitry or power source is part of a removable/replaceable module; and wherein the monitoring device is configured to periodically activate to sense for the presence of one or more chemicals regardless of whether the monitoring device is connected to the associated receiver.

2. The monitoring device of claim 1, wherein the flow conduit includes at least one of a sewer pipe, channel, trough, open or closed fluid transmission line, heating and cooling coils or other physical material that harnesses, directs or controls fluid.

3. The monitoring device of claim 1, wherein the pool includes at least one of a reservoir, holding area, storage tank, volume drum, liquid bunker, pit, pond, hole or bowl.

4. The monitoring device of claim 1, wherein the device is fixed to an interior surface or interior lining or layer of the flow conduit, or portable.

5. The monitoring device of claim 1, wherein the device is mobile within the conduit or the pool.

6. The monitoring device of claim 5, wherein the device has a density equal to or less than a density of the fluid.

7. The monitoring device of claim 6, wherein the device is tethered to the flow conduit or pool such that the device has a limited range of motion therein.

8. The monitoring device of claim 1, wherein the power source includes an antenna configured to receive energy wirelessly and supply the received energy to at least one of the detector component or the communication circuitry.

9. The monitoring device of claim 1, wherein at least one of the detector component, communication circuitry or power source is of a printed element or component.

10. The monitoring device of claim 1, wherein at least one of the detector component, communication circuitry or power source is enclosed in a housing for use in fluids.

11. The monitoring device of claim 1, wherein the sensor further determines a state of the sensor or a status of the sensor or performance of the sensor, the communication circuitry configured to transmit the state of the sensor or status of the sensor or performance of the sensor to the associated receiver.

* * * * *